United States Patent [19]

Grosrey

[11] Patent Number: 4,993,947
[45] Date of Patent: Feb. 19, 1991

[54] EQUIPMENT FOR THE TREATMENT OF DENTAL ROOTS

[75] Inventor: Jean Grosrey, Arzier, Switzerland

[73] Assignee: Meditec S.A., Geneva, Switzerland

[21] Appl. No.: 210,400

[22] Filed: Jun. 23, 1988

[30] Foreign Application Priority Data

Jul. 16, 1987 [CH] Switzerland ............... 2707/87

[51] Int. Cl.$^5$ ............................................. A61G 5/02
[52] U.S. Cl. ............................ 433/81; 433/32; 433/224
[58] Field of Search ............... 433/81, 32, 224

[56] References Cited

U.S. PATENT DOCUMENTS

| | | | |
|---|---|---|---|
| 3,079,690 | 3/1963 | Lodige | 433/81 |
| 3,871,099 | 3/1975 | Kahn | 433/224 |
| 3,919,775 | 11/1975 | Malmin | 433/81 |
| 4,021,921 | 5/1977 | Detaille | 433/81 |
| 4,247,288 | 1/1981 | Yoshii et al. | 433/81 |

FOREIGN PATENT DOCUMENTS

| | | | |
|---|---|---|---|
| 147367 | 10/1936 | Austria . | |
| 150414 | 8/1937 | Austria . | |
| 201119 | 12/1986 | European Pat. Off. | 433/81 |
| 691027 | 4/1910 | Fed. Rep. of Germany . | |
| 294164 | 1/1954 | Switzerland | 433/81 |

OTHER PUBLICATIONS

P. 83, Cavitation and Tension in Liquids, D. H. Trevena, Adam Hilger, Bristol and Philadelphia.

Primary Examiner—John J. Wilson
Attorney, Agent, or Firm—Richard Bushnell

[57] ABSTRACT

The connection piece (2), which can be fitted in a sealed manner on an opening in the pulp chamber of a tooth, comprises a liquid injector (24) and a discharge duct (25) which lead into the pulp chamber. A vacuum pump (5) is connected to the discharge duct (25) so as to produce bubbles in the liquid inside the tooth. A pressure pump (3) connected to a liquid reservoir conveys the said liquid to the injector (24) so as to produce, by means of impulsion of the said bubbles, a cavitation in the liquid inside the tooth, owing to the action of the pressure.

13 Claims, 4 Drawing Sheets

EQUIPMENT FOR THE TREATMENT OF DENTAL ROOTS

BACKGROUND OF THE INVENTION

Apparatus of various designs have already been proposed for the treatment of dental roots. Some of these apparatus (for example German Patent No. 691,027, DOS 1,072,772, Swiss Patent No. 611,508, US Patent No. 3,919,775) use, in order to introduce a cleaning or treatment liquid inside the tooth to be treated, a pipe, the outlet end of which is engaged as far as possible inside the radicular channel(s) of the tooth. However, these channels are so narrow that it is difficult, if not impossible, to reach properly the apex of the tooth with this liquid, thus resulting in unsatisfactory treatment.

In the Swiss Patent No. 603,145, a connection piece provided with a liquid supply pipe and a liquid discharge pipe is placed in a sealed manner on an opening formed in the part of the tooth located opposite the root. So as to ensure that the inside of the tooth is properly cleaned, it is proposed, in this patent, to convey the liquid into the tooth by subjecting it to periodic pulses combined with oscillations of substantially greater frequency. However, experience has shown that this solution does not permit complete cleaning of the inside of the tooth, nor ensures that the treatment or cleaning liquid fills the radicular channels completely a necessary condition, however, for thorough cleaning of the inside of the tooth.

OBJECTS OF THE INVENTION

The aim of the present invention is to provide equipment for the treatment of dental roots, which has none of the faults mentioned in connection with the known equipment.

The equipment according to the invention is as described in claim 1.

The accompanying drawing shows, by way of example, an embodiment of the equipment according to the invention.

DETAILED DESCRIPTION

Figure 1:
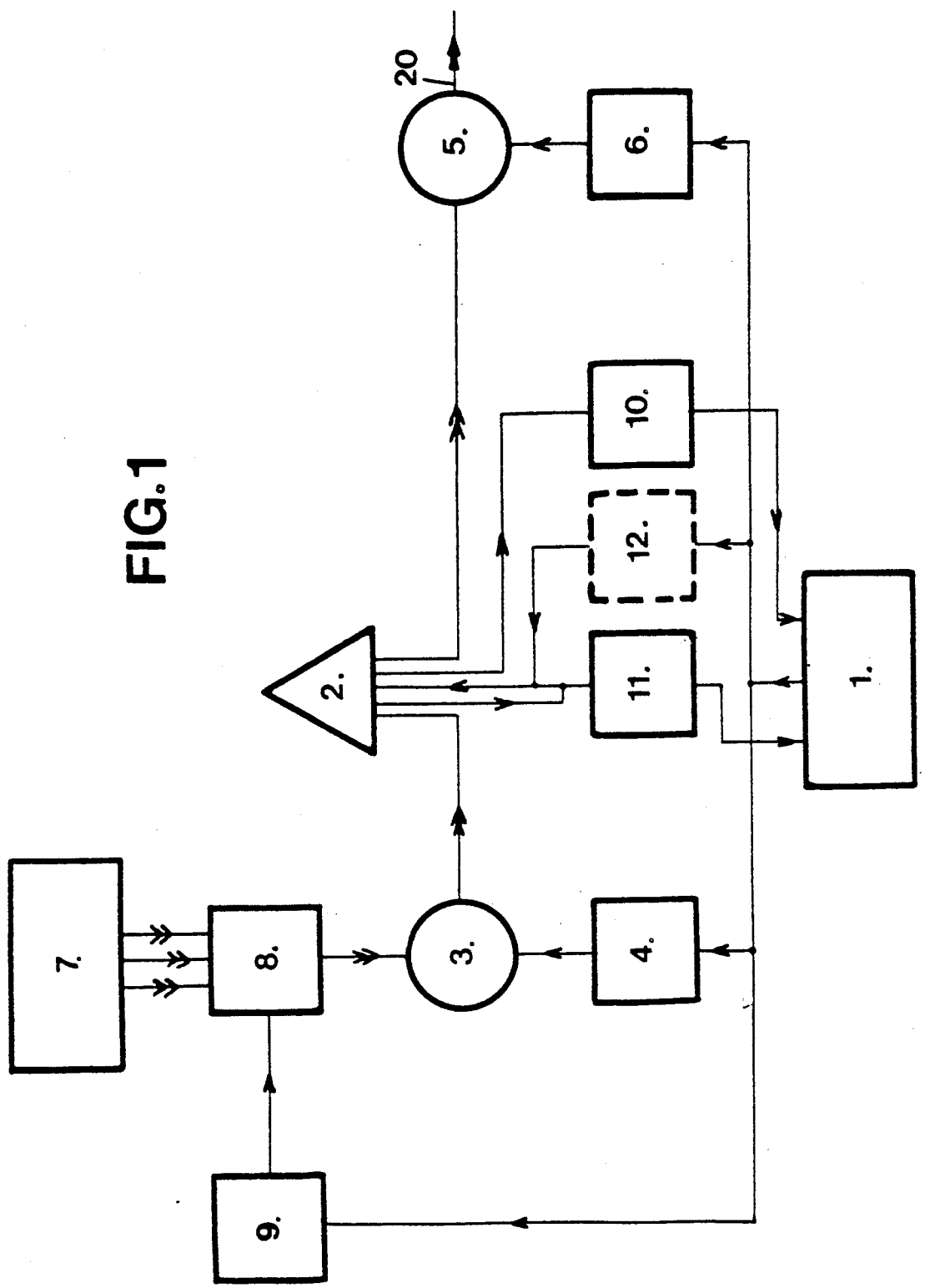
FIG. 1 is a block diagram of this equipment in its entirety.

In FIG. 1, 1 denotes a main electronic control device which controls operation during the various operating stages. 2 is a connection piece which is fitted onto the tooth to be treated. 3 is a pressure pump. 4 is a device for controlling this pump, itself controlled by the main control device 1.

5 denotes a vacuum pump and 6 a device for controlling this pump, itself controlled by 1.

The pump 3 is connected to the connection piece 2.

7 denotes a distributor for distributing the liquid products used during the various operating stages. This distributor comprises several receptacles, three for example, each containing one of these products.

8 is a switching device, with solenoid valves for example, enabling the pressure pump 3 to be selectively connected to one or other of the receptacles located at 7.

The switching device 8 is itself controlled by a switching control device 9, which is controlled by 1.

10 is a device for measuring the pressure inside the tooth, which transmits the pressure values measured to the device 1.

11 is a device for measuring the degree of attack during the cleaning stage, ie. the degree of elimination of the tooth nerve and associated vessels; it supplies its data to the device 1.

A device 12 is controlled by 1 and controls ionophoresis during the tooth disinfection stage.

In FIG. 1, the lines with a single arrow represent the commands, while the lines with a double arrow represent the flow of liquid.

Figure 2:
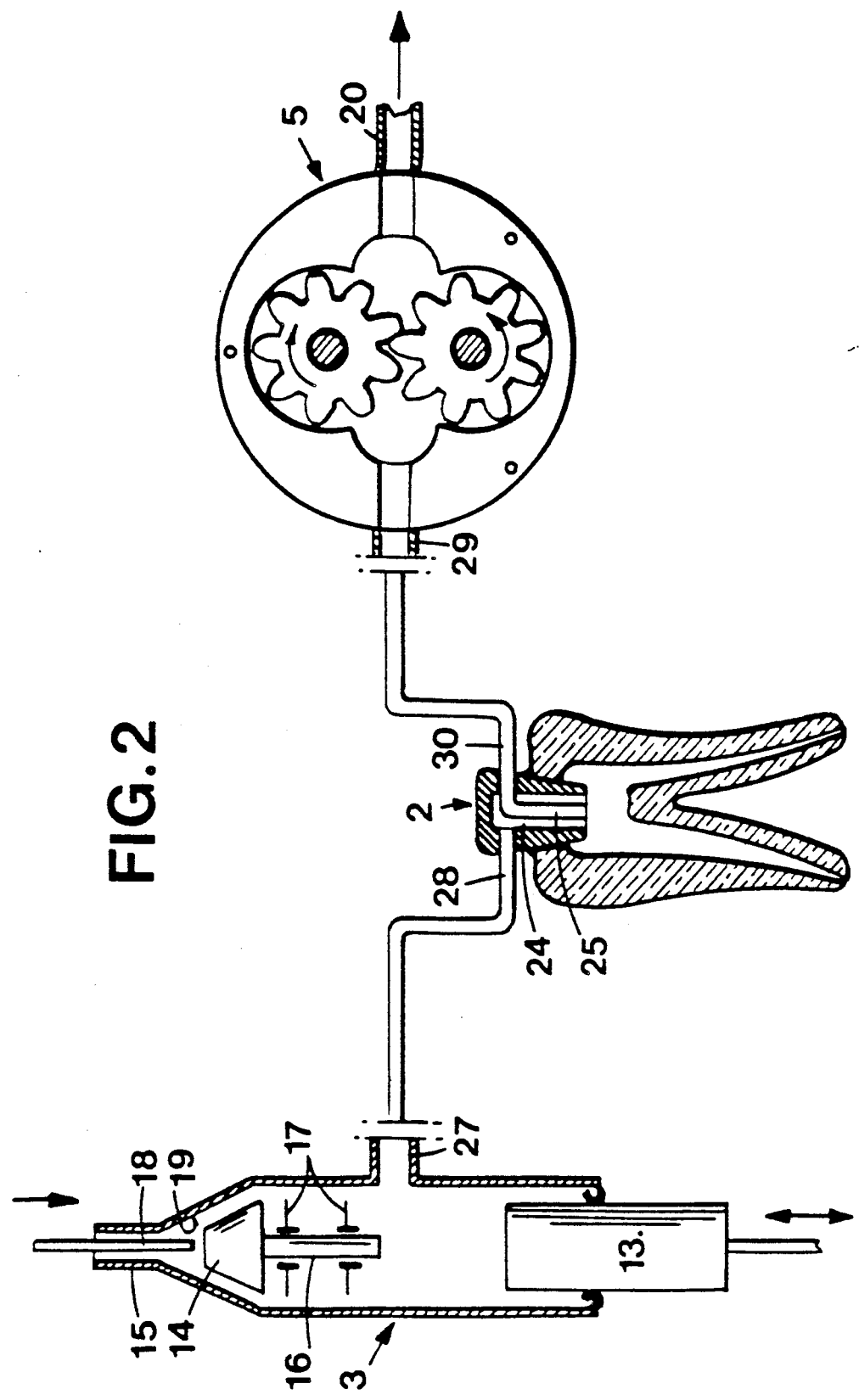
FIG. 2 is a partial schematic view showing the pressure pump, the vacuum pump and, on a larger scale, a tooth provided with the connection piece connecting these two pumps.

It can be seen in FIG. 2 that the pressure pump is a single-acting piston pump 13, with a single automatic valve 14, on the suction side 15, operated by the liquid on which the pump acts. The piston 13 is actuated by an adjustable-speed electric motor (not shown).

The valve 14 is freely movable. Its stem 16 is simply guided at 17 and, on the opposite side, there is an adjustable stop 18 which allows the valve 14 to be stopped before it reaches the closed position, ie. its fixed seat 19, so that, at the end of the closure travel, this closure is incomplete, there therefore being a small gap between the valve 14 and its seat 19, which can be adjusted according to the position given to the stop 18, as will be seen below.

The materials of the parts of the pump 3 coming into contact with the liquid must be entirely inert (stainless steel, Teflon, Viton, for example).

The vacuum pump 5 is a gear pump (FIG. 2). It parts coming into contact with the liquid are also made of an inert material (stainless steel 306L, Teflon, for example). It is driven preferably by a magnetic drive in order to eliminate the problems of tightness. Its toothed wheel must have enough play to allow adjustment of the speed and not too much to allow dry start-up. The pump outlet leads to a discharge pipe 20.

Figure 3:
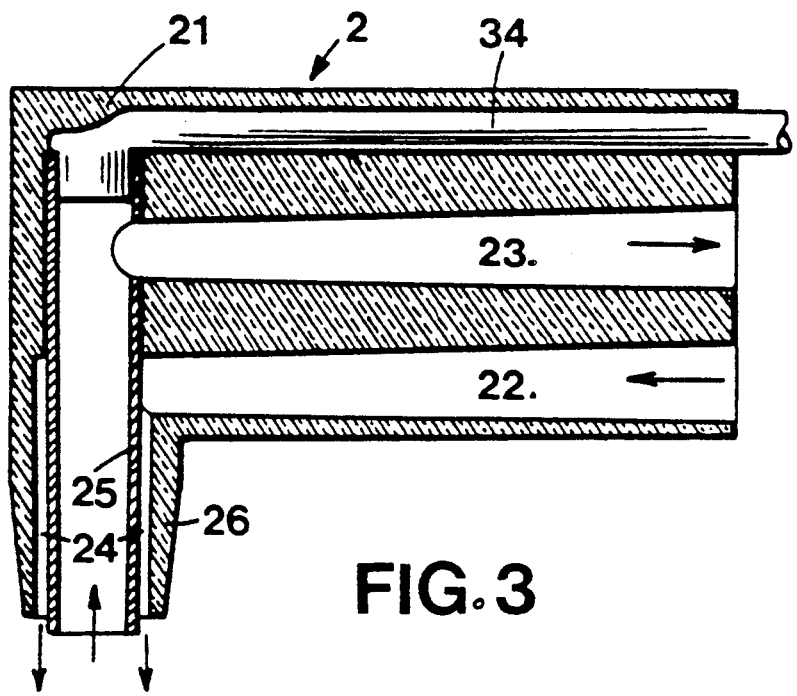
FIG. 3 is a cross-section of the connection piece.

FIG. 3 shows, on a larger scale, a crosssection of the connection piece 2. This is a body 21 which is made of molded material resistant to the liquids used and which has inside it a liquid inlet channel 22, an outlet channel 23 and an injector 24 communicating with 22. Inside the injector 24 there is a discharge duct 25 made of a metal resistant to the liquids used; 25 is coaxial with 24 and communicates with 23.

The annular injection flow cross-section, between 24 and 25, is much smaller than that of the duct 25, for example at least 10 times smaller.

The ducts 24 and 25 emerge at the end of a conical part 26 of the body 21, which is intended to be fitted in a sealed manner inside an opening formed in the end of a tooth to be treated, opposite its root. Thus these pipes emerge in the part of the pulp chamber of the tooth close to the said opening, at a distance therefore from the radicular channel(s) of the tooth.

Inside the body 21 there is one end of an electric conductor 34 which is welded to the metal discharge duct 25.

As can be seen in FIG. 2, the discharge side 27 of the pump 3 is connected to the injector 24 of the connection piece 2 (FIG. 3) by a pipe 28 fixed inside the inlet channel 22. The discharge duct 25 is connected to the inlet 29 of the pump 5 by a pipe 30 fixed inside the outlet channel 23 of the connection piece (FIGS. 2 and 3).

The product distributor 7 comprises receptacles (not shown) each containing one of the following pro physiological serum (aqueous solution containing 0.9% NaCl);

EDTA (acqueous solution containing 8% of the disodium salt of ethylenediaminetetracetic acid);

Dakin's solution (aqueous solution containing 2 to 5% NaOCl).

It is the central control device 1 which ensures, during each stage of the treatment, that the inlet side 15 of the pressure pump is connected to the required receptacle, by means of the switching device 8.

The physiological serum is used during measurement of the resistance of the interior of the tooth, as will be explained below, and during the (optional) ionophoresis stage, which will be described below, and also as a rinsing product.

Attack using EDTA (optional) is performed when it is required to enlarge radicular channels which are too narrow. This product attacks the dentine, but not the nerve tissue.

The nerve and associated vessels are attacked using Dakin's solution, during cleaning of the inside of the tooth. Dakin's solution is also used during disinfection. Attack with EDTA must be performed before attack with Dakin's solution.

This is how the equipment described functions:

The liquid from one of the receptacles of the distributor 7 is sucked in by the pump 3 when its piston 13 performs its intake stroke, ie. moves away from the valve 14 which is therefore open as a result of the suction effect due to the movement of the piston. When the piston reaches the end of its intake stroke and then moves back towards the valve 14, the latter automatically closes owing to the pressure inside the cylinder and the pump expels through its outlet 27 pressurized liquid which flows towards the connection piece 2 and enters the tooth via the injector 24.

During the whole of this cycle, the pump 5 circulates and sucks in, via the pipe 30 and the discharge duct 25, liquid located inside the tooth. The internal volume of the pipe 30 is sufficient for the liquid inside it to have an inertia opposing the acceleration of its flow, in the direction of the pump 5, during pressurization inside the tooth, and therefore during the working stroke of the pump 3. In other words, this inertia opposes the acceleration of the liquid inside the pipe 30 owing to the action of the pump 3. The liquid therefore flows inside this pipe solely owing to the action of the pump 5. Thus, rapid pressurization inside the dental cavity is ensured.

Initially, the gear pump 5 tends to create a vacuum inside the pulp chamber. In fact, the injector 24 is very delicate compared to the outlet 25. Moreover, the single-acting pump 3 is engaged in its suction stroke. As there is no outlet valve, this pump tends, while filling up, to create a vacuum inside the tooth, giving rise to the formation of bubbles filled with vapor saturated with the liquid used.

When, subsequently, the single-acting pump discharges its contents in the direction of the tooth via the fine orifice of the injector 24 (the intake valve 14 is now closed), the pressure increases very rapidly (this is due to the sudden closure of the automatic valve 14 and the inertia of the column of water contained inside the pipe 30 leading to the gear pump) and implosion of the previously formed bubbles occurs. It is known that implosion gives rise to shock effects capable of destroying, after a more or less long operation, turbine blades and, a fortiori, the nerve of a dental root.

This cavitation in the liquid inside the tooth also has the effect of forcing the liquid inside the pulp chamber to occupy the entire volume available and therefore fill the radicular channels, however narrow they may be.

The fact that inlet and outlet in the connection piece are arranged concentrically and with flowing occurring in the reverse direction facilitates the formation of bubbles inside the tooth and hence cavitation. In order to prevent the liquid crossing the apex (end of the root), the pressure is measured just at the outlet of the connection piece. This measurement will enable the speed of the vacuum pump 5 to be controlled so as to have an always slightly negative mean pressure inside the pulp chamber. This slight negative pressure will produce a temporary hyperemia in the region of the apex, which will stop the attacking action of the product (owing to dilution), in the case where the nerve must be removed. On the other hand, in the case of disinfection, it will be possible to reverse the reference of the setting so as to have a slight excess pressure which will tend to make the product used penetrate inside the tissue surrounding the root.

Figure 4:
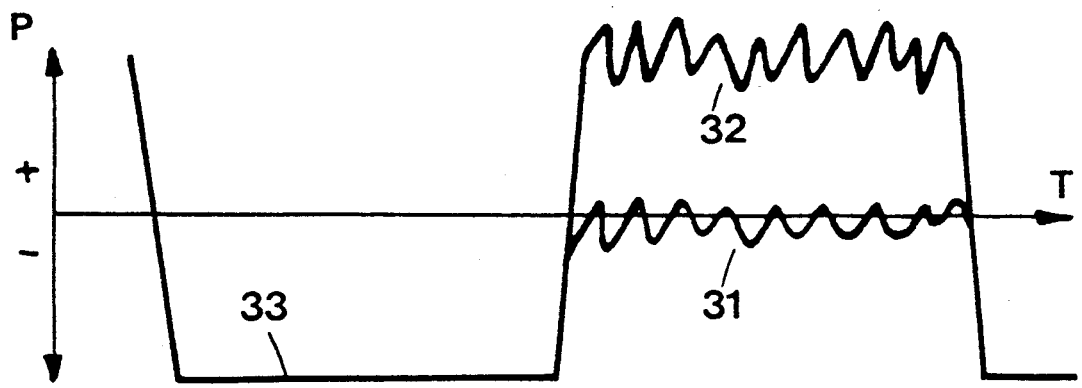
FIG. 4 is a diagram showing the pressure inside the tooth during operation of the equipment.

FIG. 4 shows the pressure, as a function of time, inside the tooth, during a cycle of the piston pump.

During attack using Dakin's solution, the line 31 can be observed, whereas, during disinfection, it is the line 32, displaced upwards by an adjustable amount, which occurs.

33 represents the vapor pressure of the liquid during the negative-pressure phase inside the tooth when the bubbles are formed.

Pressure measurement by means of the device 10 (FIG. 1) is effected by a piezo-resistive sensor (not shown). In order to lighten the part of the system which is placed inside the mouth of the patient and so that measurement can be performed nevertheless as close as possible to the pulp chamber, the pressure detector (capsule with a flexible membrane) is mounted inside a connector on the outlet tube 30 of the connection piece. A capillary tube (not shown) joins the capsule to the actual measuring device 10 which is mounted, itself, inside the apparatus, and therefore outside the patient's mouth.

The electrical signal obtained from the electronic measuring unit provides the mean pressure value. The time constant for filtering the pulses is preferably of the order of one second.

The fact that the gear pump is automatically controlled in accordance with the chosen reference pressure ensures that the gear pump performs a minimum number of revolutions so that there is always a slight negative pressure inside the tooth.

In order to control attacking of the nerve and associated vessels performed using Dakin's solution, a measurement is carried out as to the resistance between an electrode consisting of the central metal pipe 25 of the connection piece 2 (electrically connected to the conductor 34) and a damp electrode (not shown) held in the patient's hand. In order to perform this first measurement, physiological serum is injected into the root. The resistivity of the serum is the same as that of the tissues of the human body, and therefore that of the nerve still in place inside the radicular channel. This measurement is continued after switching the device 8 to Dakin's solution which has a resistivity ten times lower than that of the serum. Initially, there is an immediate drop in the resistance and then this resistance continues to decrease in accordance with progressive elimination of the nerve and hence its replacement by Dakin's solution, ie. attacking of the nerve.

The resistance measurement is performed using an alternating voltage with a square waveform, having a frequency of 500 Hz and a peak value such that the current is equal to 100 microamperes at a resistance of 4000 ohms. The voltage is kept constant, and it is the ratio between the "serum current" and the "Dakin current" which is the decisive factor for measuring the progression of attack of the nerve.

When the resistance stops decreasing, the attacking action has ended. In fact, at this point, Dakin's solution comes into contact with blood from the apex, resulting in a change in resistance.

Unlike the resistance measurement described above, in the case of ionophoresis, a direct-voltage current is applied to the same electrodes. In order to stop the attacking action, Dakin's solution was replaced with physiological serum and the pumps then stopped. Since it is now required to introduce a certain number of Coulombs into the root, the higher the current, the shorter the treatment will be. The current passing between the two electrodes will increase, controlled by the electronic control device 1. The damp electrode (anode) in the patient's hand has on it a button which allows the patient to interrupt this increase in current when the latter becomes too uncomfortable. The device 1 thus decreases the current slightly and calculates the necessary application time.

The cubic capacity of the piston pump is an important factor in the cavitation strength. There is a maximum value which must not be exceeded since, without this, it becomes difficult to control attacking of the nerve if this attacking action is too rapid. An operating time of 2 to 10 minutes is particularly suitable. A cubic capacity of 0.35 cubic centimetres, with a drive motor of the pump running at 1200 revs/minute, corresponds to such a maximum value which must not be exceeded The relative pressure of the pressure pump will be preferably between 0 and 5 bar and the relative negative pressure of the vacuum pump will be preferably variable between 0 and −0.8 bar.

The main electronic control device is able to ensure completely automatic operation of the equipment, controlled by a program. It may also operate in semi-automatic mode. In all cases, it enables the degree with which the nerve is attacked by Dakin's solution to be controlled, either by regulating the speed of the motor driving the pressure pump, or by operating the adjustable stop 18 (FIG. 2). It also enables the pressure inside the tooth to be measured, as well as automatic control of the gear pump, control of the end of the attacking action, disinfection, enlargement of the radicular channels using EDTA and disinfection by ionophoresis.

The above relates to the first stage of treatment of dental roots, ie. the complete removal of the nerve and its odontoblastic extensions together with the blood vessels ensuring its vascularization, located inside the dental cavity, as well as total disinfection of this cavity.

Figure 5:
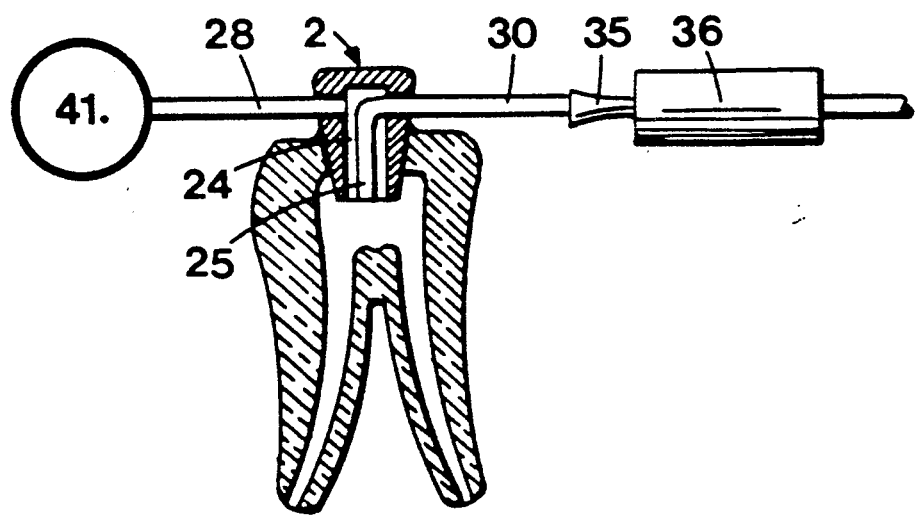
FIG. 5 indicates a modification of the equipment of FIG. 2, for effecting subsequent drying of the dental cavity.

The equipment described may also be used for the final stage in the treatment, ie. drying and filling of the dental cavity. This will now be described with reference to FIGS. 5 and 6.

After the dental pulp has been removed and eliminated and the dental cavity disinfected, as described, the pipe 30 (FIG. 2) is disconnected from the pump 5 and connected to a duct 35 itself connected to a device 36 for filtering and heating sterilized air. The pipe 28 joining the connection piece to the pump 3 (FIG. 2) is connected to a vacuum pump 41.

Figure 6:
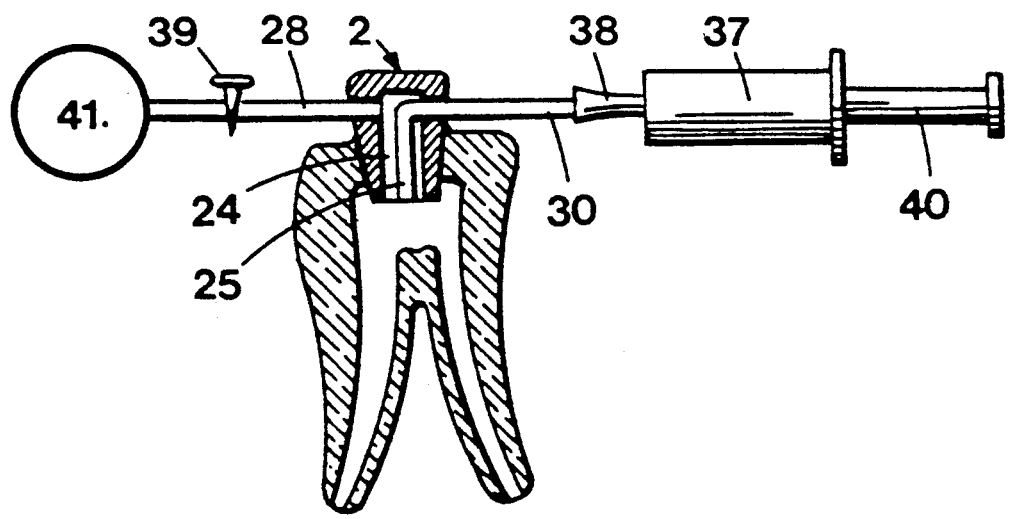
FIG. 6 illustrates a modification of the equipment of FIG. 2 for the purpose of applying a dental paste to the dental cavity following completion of the treatment and drying in accordance with the apparatus of FIGS. 2 and 5 respectively.

Once this has been done, the filtering and drying device 36 as well as the suction pump 41 are operated, for 6 minutes for example, thereby ensuring perfect drying of the dental cavity. After that, the pump 41 is stopped and the device 36 is disconnected from the pipe 30 of the connection piece 2, and a syringe 37 (for example a syringe containing insulin) is connected to the connection piece, in its place, via a pipe 38. This syringe is filled with a dental filling paste previously prepared, during the first stage of the treatment. Moreover, a Mohr pinchcock 39 is placed on the pipe 28 joining the connection piece 2 to the vacuum pump 41 (FIG. 6).

After this has been done, the vacuum pump 41 is operated so as to create a vacuum inside the dental cavity, the Mohr pinchcock being pressed for a short while (one second for example) so as to render it inoperative. As a result of the vacuum thus created inside the tooth, the paste inside the syringe 37 is sucked into the dental cavity and fills the latter completely, right into the smallest recesses. By way of precaution, a light pressure may be exerted simultaneously on the plunger 40 of the syringe cylinder 37 so as to compensate for the friction effect of the paste inside the latter.

The operation is thus completed and the connection piece is withdrawn. A radiographic test may be performed in order to check the quality of the filling.

What is claimed is:

1. Equipment for the treatment of dental roots, comprising a connection piece (2), which can be fitted in a sealed manner on an opening in the pulp chamber of a tooth, said connection piece being provided with an injector (24) connected to a supply pipe (28) for conveying liquid into the tooth, and a duct (25) for discharging the liquid located inside the tooth, wherein the injector (24) and the discharge duct (25) lead into the pulp chamber when the connection piece (2) is fitted onto a tooth, the said equipment further comprising cavitation-inducing means including a gear pump (5) having an input side connected to the discharge duct (25), so as to control the mean pressure in the liquid inside the pulp chamber and inside the radicular channel of the tooth by providing continuous suction on the chamber, and said cavitationinducing means further including a piston pump (3) connected to said supply pipe and to a reservoir containing liquid to be conveyed to the injector (24), so as to perform complete filling of the tooth with said liquid and for producing alternate phases of suction and compression so as to induce a cavitation in the liquid inside the pulp chamber and inside the radicular channel(s) of the tooth, thus completely cleansing this cavity and these channels.

2. The equipment as claimed in claim 1, wherein the part of the injector (24) and the part of the discharge duct (25) located inside the dental cavity are concentric.

3. The equipment as claimed in claim 2, wherein the said part of the injector (24) is arranged concentrically around that of the discharge duct (25) and has a region with a cross-section at least ten times smaller than that of the discharge duct.

4. The equipment as claimed in claim 1 or 3, wherein the discharge duct is connected to the pump (5) by a pipe (30) which has an internal volume large enough for the liquid inside it to have an inertia opposing the acceleration of its flow towards the gear pump (5) during pressurization inside the tooth, so as to ensure rapid pressurization producing cavitation.

5. The equipment as claimed in claim 1, wherein the piston pump (3) is a single-acting pump, with a single automatic valve (14) on the suction side.

6. The equipment as claimed in claim 1, wherein the pressure pump (3) is provided with an adjustable stop (18) designed to cooperate with the automatic valve (14) at the end of its closure travel, so as to stop at an adjustable distance from its seat (19).

7. The equipment as claimed in claim 1, and further comprising several reservoirs (7) for various liquids and switching means (8) for connecting the piston pump (3) selectively to these reservoirs.

8. The equipment as claimed in claim 7, and further comprising means (1) for controlling the flowrate and the operating time of the pump.

9. The equipment as claimed in claim 8, wherein the said means for controlling the flowrate and the operating time of the pumps are arranged so as to ensure that the mean pressure inside the pump chamber, during treatment, is always negative.

10. The equipment as claimed in claim 7, and further comprising means for controlling the switching means in accordance with a program.

11. The equipment as claimed in claim 1, and further comprising means for measuring the electrical resistance of the liquid inside the pulp chamber and the radicular channel(s), which means comprise an electrode consisting of the part of the discharge duct located inside this cavity, and another electrode intended to be placed in damp contact with the body of the patient whose tooth is being treated.

12. The equipment as claimed in claim 1, wherein the relative pressure inside the pulp chamber is variable between 0 and 0.5 bar, and wherein the relative negative pressure inside this chamber is variable between 0 and −0.8 bar.

13. The equipment as claimed in claim 1, and further comprising an air filtering and heating device (36) designed to be connected to the connection piece (2) in place of the gear pump (5) so as to ensure drying of the dental cavity, and also comprising, a syringe (37) containing dental paste, intended to be connected via a pipe (38) to the connection piece, in place of the air filtering and heating device (36), and a member (39) for closing the pipe (28) joining a vacuum pump (41) to the connection piece (2), so as to cause filling of the dental cavity with the filling paste, as a result of the vacuum created inside this cavity by said vacuum pump (41).

* * * * *